US005571903A

United States Patent [19]

Gryaznov

[11] Patent Number: 5,571,903
[45] Date of Patent: Nov. 5, 1996

[54] AUTO-LIGATING OLIGONUCLEOTIDE COMPOUNDS

[75] Inventor: Sergei M. Gryaznov, San Mateo, Calif.

[73] Assignee: Lynx Therapeutics, Inc., Hayward, Calif.

[21] Appl. No.: 89,999

[22] Filed: Jul. 9, 1993

[51] Int. Cl.⁶ ............................ C07H 21/02; C07H 21/04
[52] U.S. Cl. ................... 536/23.1; 536/24.3; 536/24.31; 536/24.5
[58] Field of Search ................................ 536/23.1, 24.1, 536/24.3, 24.31, 24.5

[56] References Cited

U.S. PATENT DOCUMENTS

| 4,739,044 | 4/1988 | Stabinsky | 536/23.1 |
| 4,958,013 | 9/1990 | Letsinger | 536/24.5 |
| 5,098,890 | 3/1992 | Gewirtz et al. | 514/44 |

FOREIGN PATENT DOCUMENTS

| PCT/US89/02649 | 12/1989 | WIPO . |
| PCT/US90/01002 | 9/1990 | WIPO . |
| PCT/US91/06143 | 3/1992 | WIPO . |

OTHER PUBLICATIONS

Shabarova et al Nucleic Acids Research, 19:4247–4251 (1991) Chemical ligation of DNA: the first non–enzymatic assembly of a biologically active gene.
Thuong et al Tetrahedron Letters, 28:4157–4160 (1987) Synthese et reactivite d'oligothymidylates subsitiues par un agent intercalant et un groupe thiophosphate.
Francois et al Proc. Natl. Acad. Sci., 86:9702–9706 (1989) Sequence–specific recognition and cleavage of duplex DNA via triple–helix formation by oligonucleotides covalently linked to a phenanthrolin–copper chelate.
Thuong et al Chapter 12 in, Eckstein, editor, Oligonucleotides and Analogues: A Practical Approach (IRL Press, Oxford, 1991) Oligonucleotides attached to intercalators, photoreactive and cleavage agents.
Gryaznov et al J. Am. Chem. Soc., 115:3808–3809 (1993) Chemical ligation of oligonucleotides in the presence and absence of a template.
Knorre et al pages 195–218 in Prospects for Antisense Nucleic Acid Therapy of Cancer and AIDS (Wiley–Liss, New York, 1991) Novel anitsense derivatives: antisense DNA intercalators, cleavers, and alkylators.
Gryaznov et al Tetrahedron Letters, 34: 1261–1264 (1993) Anchor for one step release of 3'-aminooligonucleotides from a solid support.
Gryaznov et al Nucleic Acids Research, 21:1403–1408 (1993) Template controlled coupling and recombination of oligonucleotide blocks containing thiophosphoryl groups.
Gryaznov et al Nucleic Acids Research, 20:3403–3409 (1992) Synthesis and properties of oligonucleotides containing aminodeoxythymidine units.
Roberts et al Proc. Natl. Acad. Sci., 88:9397–9401 (1991) Specificity and stringency in DNA triplex formation.

Reed et al Bioconjugate Chem., 2:217–225 (1991) Acridine– and cholesterol–derivatized solid supports for improved synthesis of 3'–modified oligonucleotides.
Zuber et al J. Am. Chem. Soc., 115: 4939–4940 (1993) Enhanced ligation of DNA with a synthetic effector molecule.
Will et al Tetrahedron Letters, 33:2729–2732 (1992) Attachment of vitamin E derivatives to oligonucleotides during solid–phase synthesis.
Letsinger et al Proc. Natl. Acad. Sci., 86:6553–6556 (1989) Cholesteryl–conjugated oligonucleotides: synthesis, properties, and activity as inhibitors of replication of human immunodeficiency virus in cell culture.
Uhlmann et al Chemical Reviews, 90:543–584 (1990) Antisense oligonucleotides: a new therapeutic principle.
Shea et al Nucleic Acids Research, 18:3777–3783 (1990) Synthesis, hybridization properties and antiviral activity of lipid–oligonucleotide conjugates.
Kabanov et al FEBS Letters, 259:327–330 (1990) A new class of antivirals: antisense oligonucleotides combined with a hydrophobic substituent effectively ihnibits influenza virus reproduction and synthesis of virus–specific proteins in MDCK cells.
Stein et al Biochemistry, 30:2439–2444 (1991) Mode of action of 5'–linked cholesteryl phosphorothioate oligonucleotides in inhibiting syncytia formation and infection by HIV–1 and HIV–2 in vitro.
Farooqui et al Bioconjugate Chem., 2:422–426 (1991) Effect of structural variations in cholesteryl–conjugated oligonucleotides on inhibitory activity towards HIV–1.
Ferris et al Nucleosides & Nucleotides, 8:407–414 (1989) N–cyanoimidazole and diimidazole imine: water–soluble condensing agents for the formation of the phosphodiester bond.
Sokolova et al FEBS Letters, 232:153–155 (1988) Chemical reactions within DNA duplexes: cyanogen bromide as an effective oligodeoxynucleotide coupling agent.
MacKellar et al Nucleic Acids Research, 20:3411–3417 (1992) Synthesis and Physical properties of anti–HIV antisense oligonucleotides bearing terminal lipophilic groups.

(List continued on next page.)

Primary Examiner—Mindy Fleisher
Assistant Examiner—David Guzo
Attorney, Agent, or Firm—Cooley Godward Castro Huddleson & Tatum

[57] ABSTRACT

The invention provides compositions and a method for delivering an antisense compound or probe to a target polynucleotide. The compositions of the invention comprise a plurality of compounds each having an oligonucleotide moiety from about 4 to 12 monomers in length whose 3' and/or 5' termini have been modified by the addition of one or more terminal binding moieties. Whenever the oligonucleotide moieties specifically anneal to a target polynucleotide in a contiguous end-to-end fashion, the terminal binding moieties are capable of spontaneously interacting with one another to form a covalent linkages or stable complexes so that an effective antisense compound or probe is formed. The invention facilitates the delivery of antisense compounds to their targets and reduces the likelihood of non-specific binding to non-target structures.

13 Claims, No Drawings

OTHER PUBLICATIONS

Fidanza et al., Introduction of Reporter Groups at Specific Sites in DNA Containing Phosphorothioate Diesters, Journal of the American Chemical Society, vol. 11, (1989), pp. 9117–9119.

Horn et al., Forks and combs and DNA: the synthesis of branched oligodeoxyribonucleotides, Nucleic Acids Research, vol. 17, No. 17, (1989), pp. 6959–6967.

Prakash et al. Structural Effects in the Recognition of DNA by Circular Oligonucleotides, Journal of American Chemical Society, vol. 114, (1992), pp. 3523–3527.

Goodchild, Conjugates of Oligonucleotides and Modified Oligonucleotides: A Review of Their Synthesis and Properties, Bioconjugate Chemistry, vol. 2, (1990), pp. 165–187.

Luebke et al., Nonenzymatic ligation of double–helical DNA by alternate–strand triple helix formation, Nucleic Acids Research, vol. 20, No. 12, (1992), pp. 3005–3009.

Rothenberg et al., Journal of the National Cancer Institute, 81:20:1539–1544, 18 Oct. 1989.

Simons et al., Nature, 359:67–70, 3 Sep. 1992.

Fahy et al. (1993) Nuc. Acids Res. 21(8), 1819–1826.

Wickstrom et al. (1988), PNAS, USA 85, 1028–1032.

AUTO-LIGATING OLIGONUCLEOTIDE COMPOUNDS

The invention relates generally to oligonucleotides and their use as diagnostic probes and therapeutic agents, and more particularly, to combinations of two or more oligonucleotides or analogs thereof that are capable of stable complexes when annealed to contiguous sites on a template.

BACKGROUND

The unpredictability and expense of conventional drug discovery has led to the exploration of several drug discovery approaches that promise more systematic and/or rapid identification candidate compounds for testing in biological assays and disease models. Examples of such approaches include selection of small peptides from a synthetic or recombinant peptide libraries, e.g. Pirrung et al, U.S. Pat. No. 5,143,854; Geysen et al, J. Immunol. Meth., 102: 259–274 (1987); Lam et al, Nature, 354: 82–84 (1991); Scott et al, Science, 249: 386–390 (1990); the construction and selection of human or humanized antibodies from recombinant antibody libraries, e.g. Riechmann et al, Nature, 332: 323–327 (1988); Winter and Milstein, Nature, 349: 293–299 (1991); selection of aptamers or ribozymes from random sequence polynucleotide libraries, e.g. Ellington and Szostak, Nature, 346: 818–822 (1990); Blackwell et al, Science, 250: 1104–1110 (1990); Tuerk et al, Science, 249: 505–510 (1990); Joyce, Gene, 82: 83–87 (1989); Cech et al, U.S. Pat. No. 4,987,071; Haseloff et al, Nature, 334: 585–591 (1988); and the use of antisense oligonucleotides, e.g. Uhlmann and Peyman, Chemical Reviews, 90: 543–584 (1990); Goodchild, Bioconjugate Chemistry, 1: 165–187 (1990); Helene et al, Biochim. Biophys. Acta, 1049: 99–125 (1990); Cohen, Ed., Oligonucleotides: Antisense Inhibitors of Gene Expression (Macmillan Press, New York, 1989); Crooke, Ann. Rev. Pharmacol. Toxicol., 32: 329–376 (1992); McManaway et al, Lancet, Vol. 335, pgs. 808–811 (1990); Bayever et al, Antisense Research and Development, 2: 109–110 (1992); Manson et al, Lymphokine Research, Vol. 9, pgs. 35–42 (1990); Lisziewicz et al, Proc. Natl. Acad. Sci., 90: 3860–3864 (1993); Miller, Biotechnology, Vol. 9, pgs. 358–362 (1991); Chiang et al, J. Biol. Chem., Vol. 266, pgs. 18162–18171 (1991); Calabretta, Cancer Research, Vol. 51, pgs. 4505–4510 (1991); and the like.

Of the cited examples, the antisense approach presents a compelling advantage of not requiring one or more initial screening steps to identify candidate compounds capable of binding to a predetermined target. Specific binding is achieved by providing an oligonucleotide or an analog thereof capable of forming a stable duplex or triplex with a target nucleotide sequence based on Watson-Crick or Hoogsteen binding, respectively. Thus, as soon as the sequence of a target polynucleotide is determined, the structure of candidate antisense compounds is also determined. The specifically bound antisense compound then either renders the respective targets more susceptible to enzymatic degradation, blocks translation or processing, or otherwise blocks or inhibits its expression or function.

Another advantage of the antisense approach has been the development of reliable and convenient methods for solid phase synthesis of polynucleotides and analogs thereof, e.g. Caruthers, Science, Vol. 230, pgs 281–285 (1985); Beaucage et al, Tetrahedron, 48: 2223–2311 (1992); and Eckstein, ed., Oligonucleotides and Analogues: A Practical Approach (IRL Press, Oxford, 1991). In particular, the availability of synthetic oligonucleotides and a variety of nuclease-resistant analogs, e.g. phosphorothioates, methylphosphonates, and the like, has further encouraged investigation of antisense compounds for treating a variety of conditions associated with the inappropriate expression of indigenous and/or exogenous genes, such as described in the references cited above.

Notwithstanding the many hurdles that have been overcome in the course of developing antisense compounds, several significant uncertainties still stand in the way of their widespread application as drugs. One such uncertainty concerns whether a sufficient concentration of antisense compound can be delivered to its target polynucleotide so that translation or transcription can be effectively shut down. This problem has led to many proposals for enhancing oligonucleotide drug delivery, e.g. Letsinger, U.S. Pat. No. 4,958,013; Latham et al, International application PCT/US91/02224; MacKellar et al, Nucleic Acids Research, 20: 3411–3417 (1992); Wagner et al, Proc. Natl. Acad. Sci., 87: 3410–3414 (1990); Citro et al, Proc. Natl. Acad. Sci., 89: 703 1–7035 (1992); Rosenberg et al, International application PCT/US92/05305. One aspect of this problem is the observation that longer oligonucleotides appear to be more difficult to deliver to cellular interiors than shorter oligonucleotides, e.g. Loke et al,; Proc. Natl. Acad. Sci., 86: 3474–3478 (1989); and Maher III et al, Nucleic Acids Research, 16: 3341–3357 (1988). On the other hand, it has also been observed that shorter antisense compounds appear to be less effective in inhibiting expression than longer antisense compounds, apparently due to the lack of stability of the shorter duplexes under physiological conditions. Thus, with current approaches, a serious trade-off exists in selecting the "best" size of antisense compound.

Another uncertainty concerns the degree of specificity of antisense oligonucleotides under physiological conditions. Antisense oligonucleotides could be non-specific in at least two senses: (i) duplex or triplex formation may lack specificity, e.g. non-perfectly matched duplexes may form—leading to the unwanted inhibition of non-target polynucleotides, and (ii) the moieties not directly involved in base pairing, e.g. the backbone or other appending groups, may interact non-specifically with other cellular components leading to undesired side effects, e.g. Woolf et al, Proc. Natl. Acad. Sci., 89: 7305–7309 (1992); Matsukura et al, Proc. Natl. Acad. Sci., 84:7706–7710 (1987); and the like. In regard to first type of nonspecificity, it has been observed that duplexes involving longer oligonucleotides tend to be more tolerant of mismatches—and hence, less specific—than duplexes involving shorter oligonucleotides, e.g. Young et al, Nucleic Acids Research, 19: 2463–2470 (1991). In regard to the second type of nonspecificity, such activity may not be surprising in view of the large body of work on the use of polyanions, in particular homopolymeric polynucleotides, as anti-viral compounds, e.g. Levy, Chapter 7, in Stringfellow, editor, Interferon and Interferon Inducers (Marcel Dekker, New York, 1980). Interestingly, increased activity—and with some polyanions increased toxicity—has been observed with increased polymer size.

Several of the problems summarized above could be obviated by the availability of a means for remotely assembling antisense compounds in situ from shorter fragments which separately could be delivered to a target polynucleotide and which would have reduced non-specific binding because of the unfavorable binding kinetics of short oligonucleotides for partially complementary sequences under physiological conditions.

SUMMARY OF THE INVENTION

The invention relates to compositions and a method for delivering an antisense compound or probe to a target polynucleotide. The compositions of the invention comprise a plurality of compounds each having an oligonucleotide moiety, preferably from about 4 to about 12 monomers in length, whose 3' and/or 5' termini have been modified by the addition of at least one terminal binding moieties. Whenever the oligonucleotide moieties specifically anneal to a target polynucleotide in a contiguous end-to-end fashion, the terminal binding moieties are capable of spontaneously interacting with one another to form an effective antisense compound or probe.

Preferably, compositions of the invention comprise from two to five components as illustrated below:

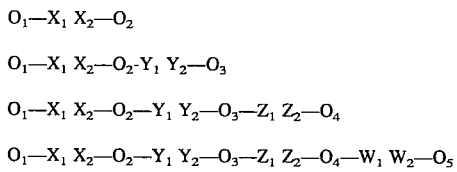

wherein $O_1$ through $O_5$ are oligonucleotide moieties and $X_1$, $X_2$; $Y_1$, $Y_2$; $Z_1$, $Z_2$, and $W_1$, $W_2$ are pairs terminal binding moieties. In accordance with the invention, upon annealing of the oligonucleotide moieties to a target polynucleotide, the terminal binding moieties of each pair are brought into juxtaposition so that they form a stable covalent linkage or non-covalent complex. The interaction of the terminal binding moieties of the one or more pairs permits the assembly of an effective antisense and/or anti-gene compound.

Definitions

The term "oligonucleotide" as used herein includes linear oligomers of natural or modified monomers or linkages, including deoxyribonucleosides, ribonucleosides, α-anomeric forms thereof, polyamide nucleic acids, and the like, capable of specifically binding to a target polynucleotide by way of a regular pattern of monomer-to-monomer interactions, such as Watson-Crick type base pairing, Hoogsteen type base pairing, or the like. Usually monomers are linked by phosphorus(V) linkages, such as phosphodiester bonds or analogs thereof, to form oligonucleotides ranging in size from a few monomeric units, e.g. 3–4, to several hundreds of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Phosphorus(V) linkages between nucleosidic monomers include phosphodiester bonds and analogs of phosphodiester bonds, such as phosphorothioate, phosphorodithioate, phosphoroselenoate, phosphorodiselenoate, phosphoroanilothioate, phosphoranilidate, and the like.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992) and analogs thereto, including synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like, to provide reactive functionalities for branch points, attachment of labeling moieties, and the like.

"Stable" in reference to the formation of a covalent linkage and/or non-covalent complex between terminal binding moieties means that melting temperature of the oligonucleotide moieties incorporating the given pair(s) of terminal binding moieties and their target polynucleotide is increased by at least twenty-five percent over the melting temperature of oligonucleotide moieties alone, wherein melting temperature is measured by standard techniques, e.g. half maximum of 260 nm absorbance v. temperature as described more fully below. Preferably, stable means that melting temperature of the oligonucleotide moieties incorporating the given pair(s) of terminal binding moieties and its target polynucleotide is increased by at least fifty percent over the melting temperature of oligonucleotide moieties alone.

"Linkage" in reference to the reaction of binding moieties includes both covalent linkages and non-covalent complexes.

DETAILED DESCRIPTION OF THE INVENTION

The invention relates to a method and compositions for in situ formation of an effective antisense compound or probe on a target polynucleotide. Compositions of the invention comprise a plurality of component compounds, preferably from two to five, each of which comprises an oligonucleotide moiety and at least one terminal binding moiety. The components of the composition assemble spontaneously upon annealing to the target polynucleotide which serves as a template for holding pairs of terminal binding moieties in juxtaposition for ligation or for the formation of non-covalent complexes. Preferably, oligonucleotide moieties of the compositions are selected so that they undergo either Watson-Crick type base pairing with single stranded polynucleotide targets or Hoogsteen or reverse Hoogsteen types of binding with double stranded target polynucleotides.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding), however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88: 9397–9401 (1991); Roberts et al, Science, 258: 1463–1466 (1992); Distefano et al, Proc. Natl. Acad. Sci., 90: 1179–1183 (1993); Mergny et al, Biochemistry, 30: 9791–9798 (1991); Cheng et al, J. Am. Chem. Soc., 114: 4465–4474 (1992); Beal and Dervan, Nucleic Acids Research, 20: 2773–2776 (1992); Beal and Dervan, J. Am. Chem. Soc., 114: 4976–4982 (1992); Giovannangeli et al, Proc. Natl. Acad. Sci., 89: 8631–8635 (1992); Moser and Dervan, Science, 238: 645–650 (1987); McShan et al, J. Biol. Chem., 267: 5712–5721 (1992); Yoon et al, Proc. Natl.

Acad. Sci., 89: 3840–3844 (1992); Blume et al, Nucleic Acids Research, 20: 1777–1784 (1 992); and the like.

Selection of particular oligonucleotide sequences for triplex formation can also be carried out empirically, for example, through aptamer screening, or like process, where candidate oligonucleotide moieties are selected on the basis of binding strength to an immobilized double stranded target, e.g. Ellington and Szostak, Nature, 346: 818–822 (1990); Toole et al, International application PCT/US92/01383, and the like.

Preferably, stability of terminal binding moieties are measured by determining the enhancement of strand melting temperature as compared to the melting temperature of equivalent oligonucleotide strands without terminal binding moieties. Melting temperature is measured by conventional means, e.g. by measuring strand dissociation kinetics. Generally, the temperature of fifty percent strand dissociation is taken as the melting temperature, $T_m$, which is also a convenient measure of stability. $T_m$ measurements are typically carried out in a saline solution at neutral pH with target and test oligonucleotide concentrations at between about 1.0–2.0 µM. Typical conditions are as follows: 150 mM NaCl and 10 mM $MgCl_2$ in a 10 mM sodium phosphate buffer (pH 7.0) or in a 10 mM Tris-HCl buffer (pH 7.0); or like conditions. Data for melting curves are accumulated by heating a sample of the oligonucleotide clamp/target polynucleotide complex from room temperature to about 85°–90° C. As the temperature of the sample increases, absorbance of 260 nm light is monitored at 1° C. intervals, e.g. using a Cary (Australia) model 1E or a Hewlett-Packard (Palo Alto, Calif.) model HP 8459 UV/VIS spectrophotometer and model IIP 89100A temperature controller, or like instruments.

The oligonucleotide moieties of the invention are synthesized by conventional means on a commercially available automated DNA synthesizer, e.g. an Applied Biosystems (Foster City, Calif.) model 380B, 392 or 394 DNA/RNA synthesizer. Preferably, phosphoramidite chemistry is employed, e.g. as disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. For therapeutic use, nuclease resistant backbones are preferred. Many types of modified oligonucleotides are available that confer nuclease resistance, e.g. phosphorothioate, phosphorodithioate, phosphoramidate, or the like, described in many references, e.g. phosphorothioates: Stec et al, U.S. Pat. No. 5,151,510; Hirschbein, U.S. Pat. No. 5, 166,387; Bergot, U.S. Pat. No. 5,183,885; phosphoramidates: Froehler et al, International application PCT/US90/03138; and for a review of additional applicable chemistries: Uhlmann and Peyman (cited above). In some embodiments it may be desirable to employ P-chiral linkages, in which case the chemistry disclosed by Stec et al, European patent application 92301950.9, may be employed.

The overall length of the oligonucleotide moieties, i.e. the length of the composition with all the oligonucleotide moieties lined up end-to-end, is sufficiently large to ensure that specific binding will take place only at the desired target polynucleotide and not at other fortuitous sites. Preferably, the lengths of individual oligonucleotide moieties are in the range of about 4 to about 14 nucleotides, and more preferably, in the range of about 6 to about 10 nucleotides. Preferably, the overall length of the oligonucleotide moieties in a particular composition in the range of about 12 to about 40 nucleotides, and more preferably, in the range of about 16 to 30 nucleotides.

A variety of terminal binding moieties are suitable for use with the invention. Generally, they are employed in pairs, which for convenience here will be referred to as X and Y. X and Y may be the same or different. Whenever the interaction of X and Y is based on the formation of stable hydrophobic complex, X and Y are lipophilic groups, including alkyl groups, fatty acids, fatty alcohols, steroids, waxes, fat-soluble vitamins, and the like. Further exemplary lipophilic binding moieties include glycerides, glyceryl ethers, phospholipids, sphingolipids, terpenes, and the like. In such embodiments, X and Y are preferably selected from the group of steroids consisting of a derivatized perhydrocyclopentanophenanthrene nucleus having from 19 to 30 carbon atoms, and 0 to 6 oxygen atoms; alkyl having from 6 to 16 carbon atoms; vitamin E; and glyceride having 20 to 40 carbon atoms. Preferably, a perhydrocyclopentanophenanthrene-based moiety is attached through the hydroxyl group, either as an ether or an ester, at its $C_3$ position. It is understood that X and Y may include a linkage group connecting it to an oligonucleotide moiety. For example, glyceride includes phosphoglyceride, e.g. as described by MacKellar et al, Nucleic Acids Research, 20: 3411–3417 (1992), and so on. It is especially preferred that lipophilic moieties, such as perhydrocyclopentanophenanthrene derivatives, be linked to the 5' carbon and/or the 3' carbon of an oligonucleotide moiety by a short but flexible linker that permits one lipophilic moiety to interact with another lipophilic moiety on another oligonucleotide moiety. Such linkers include phosphate (i.e. phosphodiester), phosphoramidate, hydroxyurethane, carboxyaminoalkyl and carboxyaminoalkylphosphate linkers, or the like. Preferably, such linkers have no more than from 2 to 8 carbon atoms.

Terminal binding moieties can be attached to the oligonucleotide moiety by a number of available chemistries. Generally, it is preferred that the oligonucleotide be initially derivatized at its 3' and/or 5' terminus with a reactive functionality, such as an amino, phosphate, thiophosphate, or thiol group. After derivatization, a hydrophilic or hydrophobic moiety is coupled to the oligonucleotide via the reactive functionality. Exemplary means for attaching 3' or 5' reactive functionalities to oligonucleotides are disclosed in Fung et al, U.S. Pat. No. 5,212,304; Connolly, Nucleic Acids Research, 13: 4485–4502 (1985); Tino, International application PCT/US91/09657; Nelson et al, Nucleic Acids Research, 17: 7187–7194 (1989); Stabinsky, U.S. Pat. No. 4,739,044; Gupta et al, Nucleic Acids Research, 19: 3019 (1991); Reed et al, International application PCT/US91/06143; Zuckerman et al, Nucleic Acids Research, 15: 5305 (1987); Eckstein, editor, Oligonucleotides and Analogues: A Practical Approach (IRL Press, Oxford, 1991); Clontech 1992/1993 Catalog (Clontech Laboratories, Palo Alto, Calif.); and like references.

Preferably, whenever X and Y form a covalent linkage, or bridge, X and Y pairs must react specifically with each other when brought into juxtaposition, but otherwise they must be substantially unreactive with chemical groups present in a cellular environment. Preferably, the linkages are formed by reacting phosphorothioate, or phosphorodithioate groups on one oligonucleotide moiety with haloacyl- or haloalkylamimo groups on another juxtaposed oligonucleotide moiety to form a thio- or dithiophosphorylacyl or a thio- or dithiophosphorylalkyl linkage. Generally, such linkages have the following form:

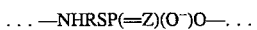

wherein R is alkyl or acyl and Z is sulfur or oxygen. The assembly reaction may involve from 2 to 10 components depending on the particular embodiment; but preferably, it involves from 2 to 5 components; and more preferably, it involves from 2 to 3 components. Preferably, the haloacyl- or haloalkylamino groups are haloacetylamino groups; and more preferably, the haloacetylamino groups are bromoacetylamino groups. The acyl or alkyl moieties of the haloacyl- or haloalkylamino groups contain from 1 to 12 carbon atoms; and more preferably, such moieties contain from 1 to 8 carbon atoms. The reaction may take place under in wide range of solvent systems; but generally, the assembly reaction takes place under liquid aqueous conditions or in a frozen state in ice, e.g. obtained by lowering the temperature of a liquid aqueous reaction mixture. Alternatively, formation of thiophosphorylacetylamino bridges in DMSO/H$_2$O has been reported by Thuong et al, Tetrahedron Letters, 28: 4157–4160 (1987); and Francois et al, Proc. Natl. Acad. Sci., 86: 9702–9706 (1989). Typical aqueous conditions include 4 µM of reactants in 25 mM NaCl and 15 mM phosphate buffer (pH 7.0). Clearly, some of the above embodiments are primarily suited for use as probes or diagnostic compounds.

Most preferably, when one of X or Y is phosphorothioate, the other is haloacetyl. Most preferably, whenever one of X or Y is phosphorothioate, the other is bromoacetyl. These binding moieties form a covalent thiophosphoylacetylamino bridge, as shown below, selectively and efficiently at low concentrations, e.g. less than one µM, when reacted in an aqueous environment in the presence of a target polynucleotide:

5'-N$_1$N$_2$N$_3$...N$_j$—NHC(=O)CH$_2$X +

1

S—P(=O)(O$^-$)O—N$_1$N$_2$N$_3$...N$_k$-3'   ⟶

2

N$_1$N$_2$N$_3$...N$_j$—NHC(=O)CH$_2$SP(=O)(O$^-$)O—N$_1$N$_2$N$_3$...N$_k$ wherein X is halo and N$_1$, N$_2$,...N$_j$ and N$_k$ are nucleotides of a j-mer and k-mer, respectively. Compound 1 can be prepared by reacting N-succinimidyl haloacetate in N,N-dimethylformamide (DMF) with a 3'-aminodeoxyribonucleotide precursor in a sodium borate buffer at room temperature. After about 35 minutes the mixture is diluted (e.g. with H$_2$O), desalted and, purified, e.g. by reverse phase HPLC. The 3'-aminodeoxyribonucleotide precursor can be prepared as described in Gryaznov and Letsinger, Nucleic Acids Research, 20: 3403–3409 (1992) or Tetrahedron Letters, 34: 1261–1264 (1993). Briefly, after deprotection, the 5' hydroxyl of a deoxythymidine linked to a support via a standard succinyl linkage is phosphitylated by reaction with chloro-(diisopropylethylamino)-methoxyphosphine in an appropriate solvent, such as dichloromethane/diisopropylethylamine. After activation with tetrazole, the 5'-phosphitylated thymidine is reacted with a 5'-trityl-O-3'-amino-3'-deoxynucleoside to form a nucleoside-thymidine dimer wherein the nucleoside moieties are covalently joined by a phosphoramidate linkage. The remainder of the oligonucleotide is synthesized by standard phosphoramidite chemistry. After cleaving the succinyl linkage, the oligonucleotide with a 3' terminal amino group is generated by cleaving the phosphoramidate link by acid treatment, e.g. 80% aqueous acetic acid for 18–20 hours at room temperature. 5'-trityl-O-3'-amino-3'-deoxynudeosides may be synthesized in accordance with Glinski et al, J. Chem. Soc. Chem. Comm., 915–916 (1970): Miller et al, J. Org. Chem. 29: 1772 (1964); Zielinki and Orgel, Nucleic Acids Research, 13: 2469–2484 (1985) and 15: 1699–1715 (1987): Ozols et al, Synthesis, 7: 557–559 (1980); and Azhayev et al, Nucleic Acids Research, 6: 625–643 (1979); which references are incorporated by reference.

5' monophosphorothioate 2 is formed as follows: A 5' monophosphate is attached to the 5' end of an oligonucleotide either chemically or enzymatically with a kinase, e.g. Sambrook et al, Molecular Cloning: A Laboratory Manual, 2nd Edition (Cold Spring Harbor Laboratory, New York, 1989). Preferably, as a final step in oligonucleotide synthesis, a monophosphate is added by chemical phosphorylation as described by Horn and Urdea, Tetrahedron Lett., 27: 4705 (1986) (e.g. using commercially available reagents such as 5' Phosphate-ON™ from Clontech Laboratories (Palo Alto, Calif.)). The 5'-monophosphate is then sulfurized using conventional sulfurizing agents, e.g. treatment with a 5% solution of S$_8$ in pyridine/CS$_2$ (1:1, v/v, 45 minutes at room temperature); or treatment with sulfurizing agent described in U.S. Pat. Nos. 5,003,097; 5,151,510; or 5,166,387. Preferably, the haloacetylamino derivatized oligonucleotides are synthesized separately from unprotected monophosphorothioate groups.

Likewise to the above, a 5'-haloacetylamino derivatized oligonucleotide 3 is reacted with a 3'-monophosphorothioate oligonucleotide 4 according to the following scheme:

3'-N$_1$N$_2$N$_3$...N$_j$(5')—NHC(=O)CH$_2$X +

3

S—P(=O)(O$^-$)O—(3')N$_1$N$_2$N$_3$...N$_k$-5'   ⟶

4

3'-N$_1$N$_2$N$_3$...N$_j$—NHC(=O)CH$_2$SP(=O)(O$^-$)O—N$_1$N$_2$N$_3$...N$_k$-5' wherein the symbols are defined the same as above, except that the nucleotides monomers of the j- and k-mers are in opposite orientations. In this case, Compound 3 can be prepared by reacting N-succinimidyl haloacetate in N,N-dimethylformamide (DMF) with a 5'-aminodeoxyribonucleotide precursor in a sodium borate buffer at room temperature, as described above for the 3'-amino oligonucleotide. 5'-aminodeoxynucleosides are prepared in accordance with Glinski et al, J. Chem. Soc. Chem. Comm., 915–916 (1970); Miller et al, J. Org. Chem. 29: 1772 (1964); Ozols et al, Synthesis, 7: 557–559 (1980); and Azhayev et al, Nucleic Acids Research, 6: 625–643 (1979); which are incorporated by reference.

The 3'-monophosphorothioate oligonucleotide 4 can be prepared as described by Thuong and Asseline (cited above).

Preferably, in compositions of the invention comprising 3 or more components, such as exemplified by the following three component composition:

O$_1$—X$_1$ X$_2$—O$_2$—Y$_1$ Y$_2$—O$_3$ the components with two terminal binding moieties, i.e. X$_2$—O$_2$—Y$_1$, have the same terminal binding moieties on both the 3' and 5' ends of the oligonucleotide moiety. This is primarily for ease of synthesis, particularly in the case of pairs consisting of phosphorothioate or phosphorodithioate and haloacyl- or haloalkylamino. Thus, in the above embodiment, X$_2$ and Y$_1$ are either both phosphorothioate or phosphorodithioate, or they are both haloacyl- or haloalkylamino.

Compounds of the invention can be employed as diagnostic probes to detect the presence of one or more target polynucleotides in a wide range of samples, including environmental samples, e.g. from public water supplies, samples from foodstuffs, and from other biological samples, such as blood, saliva, semen, amniotic fluid, tissue homogenates of plants or animals, or of human patients, and the like. The use of nucleic acid probes in human diagnostics, forensics, and genetic analysis has been extensively reviewed. For example, the following references describe many diagnostic applications of nucleic acid probes for which the present invention can be usefully employed: Caskey, Science 236: 1223–1228 (1987); Landegren et al, Science, 242: 229–237 (1988); and Arnheim et al, Ann. Rev. Biochem., 61: 131–156 (1992). Moreover, there is extensive guidance in the literature concerning the selection of hybridization conditions, labeling means, and the like, which is applicable to the practice of the present invention, e.g. Wallace et al, Nucleic Acids Research 6: 3543–3557 (1979); Crothers et al, J. Mol. Biol. 9: 1–9 (1964); Gotoh, Adv. Biophys. 16: 1–52 (1983); Wetmet, Critical Reviews in Biochemistry and Molecular Biology 26: 227–259 (1991); Breslauer et al, Proc. Natl. Acad. Sci. 83: 3746–3750 (1986); Wolf et al, Nucleic Acids Research, 15: 2911–2926 (1987); McGraw et al, Biotechniques, 8: 674–678 (1990), and the like.

Whenever compositions of the invention are employed as probes or in diagnostic assays, or in other processes not requiring direct contact with a patient, a wider range of terminal binding moieties may be employed than would be possible for therapeutic use. In diagnostic and other non-therapeutic applications, reaction of the terminal binding moieties may involve an activation step wherein one or both of the binding moieties are activated or rendered reactive towards one another by exposure to an activating agent or condensing agent, such as radiation, a reducing agent, an oxidizing agent, or the like. Exemplary, terminal binding moieties employing activating agents include thiophosphoryl groups in the presence of $K_3Fe(CN)_6$ or $KI_3$, e.g. Gryaznov and Letsinger, Nucleic Acids Research, 21: 1403–1408 (1993); phosphoryl and hydroxyl in the presence of N-cyanoimidazole, e.g. Luebke et al, J. Am. Chem. Soc., 113: 7447–7448 (1991); phosphoryl or amino group and hydroxyl in the presence of cyanogen bromide, e.g. Sokolova et al, FEBS Letters, 232: 153–155 (1988); phosphoryl and hydroxyl groups in the presence of spermine-5-(N-ethylimidazole)carboxamide and cyanoimidazole, e.g. Zuber et al, J. Am. Chem. Soc., 115: 4939–4940 (1 993); thiol and haloacyl- or haloalkylamino in the presence of pH 8–9, and the like.

Generally, use of the compositions of the invention as molecular probes comprises (i) contacting the compound(s) with a sample in a hybridization buffer, described more fully below, (ii) separating specifically bound compound from nonspecifically bound or excess composition, and (iii) detecting a signal generated directly or indirectly by the specifically bound composition. These steps are well known in art, but require routine optimization of such parameters as salt concentration, temperature, blocking agents, and the like, for particular embodiments. Preferably, the concentrations of the oligonucleotide moieties of the composition are in about 10- to 100-fold molar excess of the target polynucleotide.

Kits incorporating compositions of the invention can take a variety of forms depending on the particular embodiment, the type of assay format employed, and the labeling scheme employed. In one aspect, kits of the invention comprise a branched polymer specific for a given target molecule, a hybridization buffer, and a labeling means. A hybridization buffer is a saline solution of about 100 mM to about 1M NaCl, or its equivalent, generally buffered at neutral pH, e.g. pH 7–8. A hybridization buffer may also contain additional components such as detergents, surfactants, chelating agents, carrier compounds, e.g. bovine serum albumin, blocking agents, as described below, and the like. Kits of the invention may further comprise wash buffers for removing unbound label and/or oligonucleotide moieties, solid phase supports such as derivatized magnetic beads, or the like; and prehybridization buffers containing blocking agents, e.g. Denhardt's solution, sonicated salmon sperm DNA, detergents such as 1% SDS, or the like, for minimizing nonspecific binding of oligonucleotide moieties. An exemplary hybridization buffer comprises the following reagents: 100 mM NaCl, 10 mM $MgCl_2$, and 10 mM Tris-HCl (pH 7.0).

Preferably, compositions of the invention are employed as components of pharmaceutical compositions. A variety of diseases and disorders can be treated by administration of a composition comprising compounds of the invention. Viral diseases that can be treated by antisense inhibition of nucleic acid expression include, but are not limited to, those caused by hepatitis B virus, cytomegalovirus, herpes simplex virus I or II, human immunodeficiency virus type I or II, influenza virus, respiratory syncytial virus, and human papilloma virus. Malignancies which can be treated by administration of antisense compounds of the invention include those known to be directly or indirectly caused by the inappropriate expression of one or more genes, such as cancers caused by the inappropriate expression of oncogenes, e.g. myb, bcr-abl, kit, myc, ras, raf, abl, or the like. In such diseases, the compounds of the invention are specifically targeted to the aberrantly expressed genes associated with the diseases, or to regulatory polynucleotides that interact with aberrantly transcribed or expressed genes, e.g. Aaronson, Science, Vol. 254, pgs. 1146–1153 (1991). Acute inflammatory and immune reactions, such as septic shock, eosinophilia, and the like, can also be treated with compounds of the invention, wherein inappropriately and/or aberrantly expressed cytokine genes are inhibited, e.g. Tracey et al, Nature, Vol. 330, pgs. 662–664 (1987), U.S. Pat. No. 5,055,447, and Waage et al, J. Exp. Med., Vol. 169, pgs. 333–338 (1989)(antisense TNF-α and/or TNF-β); Starnes et al, J. Immunol., Vol. 145, pgs. 4185–4191 (1990), and Fong et al, J. Immunol., Vol. 142, pgs. 2321–2324 (antisense IL-6); Coffman et al, Science, Vol.245 pgs. 308–310 (antisense IL-5); Finkelman et al, J. Immunol., Vol. 141, pgs. 2335–2341 (1988) (antisense IL-4); Young et al, Blood, Vol. 68, pgs. 1178–1181 (1986) (antisense GM-CSF); and the like.

The components included in pharmaceutical compositions of the invention depend on several factors, including the nature of the disease or condition being treated, the location of disease lesions, the mode of drug delivery and/or administration contemplated, the latter of which can include in vivo administration by way of regional or systemic perfusion, topical application, intranasal administration, administration by implanted or transdermal sustained release systems, and the like, as well as ex vivo administration for use in bone marrow purging. A preferred method of administrating compositions of the invention comprises either regional or systemic perfusion. According to a method of regional perfusion, the afferent and efferent vessels supplying the extremity containing a lesion, e.g. a cancerous lesion, are isolated and connected to a low-flow perfusion pump in continuity with an oxygenator and heat exchanger. The iliac vessels may be used for perfusion of the lower extremities. The axillary vessels are cannulated high in the axilla for upper extremity lesions. A pharmaceutical composition containing a composition of the invention is added to the perfusion circuit, and the perfusion is continued for an appropriate time period, e.g. an hour. Perfusion rates of from 100 to 150 ml/minute may be employed for lower extremity lesions, while half that rate should be employed for upper extremity lesions. Systemic heparinization may be used throughout the perfusion, and reversed after the perfusion is complete. This isolation perfusion technique permits administration of higher dosed of chemotherapeutic agent than would otherwise be tolerated upon infusion into the arterial or venous systemic circulation.

For systemic infusion, the composition of the invention are preferably delivered via a central venous catheter, which is connected to an appropriate continuous infusion device. Indwelling catheters provide long term access to the intravenous circulation for frequent administrations of drugs over extended periods of time.

Generally a pharmaceutical composition of the invention facilitates the delivery of an effective amount of the active drug to a desired site in a manner consistent with patient safety and comfort. An effective amount of a composition of the invention depends on several factors, including the disease or condition being treated, the method of administration, the scheduling of the administration, the condition of the patient, and the like. Typically, a parentially administered dose will be in the range of about 1 µg/kg/day to about 100 mg/kg/day of patient body weight. A key factor in selecting an appropriate dose for a given condition or disease is the therapeutic result, as measure by standard criteria well known to the medical practitioner, e.g. for oncological applications see: Cancer: Principles and Practice of Oncology, 3rd Edition, edited by V. T. DeVita et al (Lippincott Company, Philadelphia, 1989).

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. For example, in water soluble formulations the pharmaceutical composition preferably includes a buffer such as a phosphate buffer, or other organic acid salt, preferably at a pH of between about 7 and 8. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g. Remington's Pharmaceutical Science, latest edition (Mack Publishing Company, Easton, Pa.).

Compounds of the invention include the pharmaceutically acceptable salts thereof, including those of alkaline earths, e.g. sodium or magnesium, ammonium or $NX_4^+$, wherein X is $C_{1-4}$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

Sustained release systems suitable for use with the pharmaceutical compositions of the invention include semipermeable polymer matrices in the form of films, microcapsules, or the like, comprising polylactides, copolymers of L-glutamic acid and gamma-ethyl-L-glutamate, poly(2-hydroxyethyl methacrylate), and like materials. Sustained release systems also include liposomally entrapped oligonucleotide clamps, e.g. as described in Liposome Technology, Vol. II, Incorporation of Drugs, Proteins, an Genetic Material (CRC Press).

EXAMPLES

Example 1

Synthesis of Two-component Composition with Cholesterol Terminal Binding Moieties A two-component composition was synthesized consisting of a first oligonucleotide moiety with a 3' cholesterol as a terminal binding moiety and a second oligonucleotide moiety with a 5' cholesterol as a terminal binding moiety. The oligonucleotide moieties were specific for the transcription product of the bcr-abl break point junction of the Philadelphia chromosome-positive leukemia cell line BV178, disclosed by Pegoraro et al, J. Natl. Canc. Inst., 70: 447 (1983). Growth of the cell line depends of the expression of the bcr-abl gene; thus it provides a convenient assay for the effectiveness of antisense compounds specific for the bcr-abl gene or gene product. The composition is defined by the following formulas SEQ ID NO: 1 and 2:

5'-CGCTGAAGGGCT(3')-Chol Chol-(5')TCTTCCTTATTGAT-3' where "Chol" represents cholesterol. The 3' cholesterol was attached to the first oligonucleotide moiety by first constructing a cholesterol-derivatized solid phase support followed by routine oligonucleotide chain extension via phosphoramidite monomers on a conventional automated DNA synthesizer (Applied Biosystems model 394). The 5' cholesterol was attached to the second oligonucleotide moiety in the final coupling step of a conventional oligonucleotide synthesis by reacting cholesterol chloroformate with the terminal nucleotide having a 5' amino group or by coupling a cholesterol phosphoramidite with a terminal hydroxyl group, the former method usually giving higher yields.

(1) A polymer supported oligonucleotide, 1 µmole scale, with terminal 5'-amino group was treated with 2 ml of a 10% solution of cholesteryl formate in chloroform/diisopropylethylamine (9:1, v:v) for 20 minutes at room temperature. The polymer support was then washed with chloroform and acetonitrile, cleaved and deprotected with concentrated ammonium (5 hours at 55° C.), and purified by reverse phase HPLC.

(2) A polymer supported oligonucleotide, 1 µmole scale, with terminal hydroxyl group was treated with 250 µl of 0.1M solution of cholesterol phosphoramidite in chloroform and 250 µl of 0.45M solution of tetrazole in acetonitrile for 10–15 minutes at room temperature. The polymer support was then washed with acetonitrile, cleaved and deprotected with concentrated ammonium (5 hours at 55° C.), and purified by reverse phase HPLC.

Each component of the above composition as well as the composition itself were administered to BV178 cells in culture. The component oligonucleotides had no effect on cell growth, but the composition substantially inhibited growth indicating an antisense effect.

Example 2

Synthesis of Two-component Composition having Bromoacetyl/phosphorothioate Terminal Binding Moieties The following components were synthesized by the procedures described. As with Example 1, the oligonucleotide moieties are specific for the bcr-abl break point junction of cell line BV178 SEQ ID NO: 1 and 2.

5'-BrCH$_2$C(=O)NH—TCTTCCTTATTGAT-3'

3'-SP(=O)(O$^-$)TCGGGAAGTCGC-5'

5'-bromoacetylamino oligonucleotide was prepared as follows: 15 μL of 0.4M N-succinimidyl bromoacetate (e.g. Calbiochem) in N,N-dimethylformamide (DMF) was added to 4.9 A$_{260}$ units of a 5'-amino-oligonucleotide precursor in 10 mL of 0.2M sodium borate buffer at room temperature. After about 35 minutes the mixture was diluted (0.5 mL H$_2$O), desalted by gel filtration on a NAP-5 column (Pharmacia), purified by reverse phase HPLC (as described below), and again desalted to yield 4 A$_{260}$ units of 5'-bromoacetylamino oligonucleotide (elution time for reverse phase HPLC, 17.4 minutes; ion exchange HPLC, 17.4 minutes). Ion exchange HPLC was carried out on a Dionex Omni Pak NA100 4×250 mm column at pH 12 (0.001M NaOH) with a 2%/minute gradient of 1.0M NaCl in 0.01M NaOH. Reverse phase HPLC was carried out on a Hypersil ODS 4.6×200 mm column with a 1%/minute gradient of acetonitrile in 0.03M triethylammonium acetate buffer, pH 7.0. A 5'-amino-oligonucleotide was prepared as described above. The 3' phosphorothioate oligonucleotide is formed as described above.

Each component of the above composition as well as the composition itself were administered to BV173 cells in culture. The component oligonucleotides had no effect on cell growth, but the composition substantially inhibited growth indicating an antisense effect.

I claim:

1. A polynucleotide binding composition comprising:
   two to five components with an overall length of 12 to 120 nucleotides, each component comprising:
   (1) an oligonucleotide moiety comprising at least 6 nucleotides, and
   (2) at least one terminal binding moiety linked by a short flexible linker having no more than from 2 to 8 carbon atoms to a 5' or 3' terminus of said oligonucleotide moiety,
   each terminal binding moiety being a member of a pair of terminal binding moieties that spontaneously forms a stable non-covalent complex with one another when said components of said composition specifically bind to a target polynucleotide in a contiguous end-to-end fashion such that each pair of terminal binding moieties is brought into juxtaposition.

2. The polynucleotide binding composition of claim 1 wherein the number components is in the range of from 2 to 3 and wherein said oligonucleotide moiety of each component has a length in the range of from 6 to 40 monomers.

3. The polynucleotide binding composition of claim 1 selected from the group of polynucleotide binding compositions defined by the formulas:

$$O_1—X_1\ X_2—O_2,$$

$$O_1—X_1\ X_2—O_2—Y_1\ Y_2—O_3,$$

$$O_1—X_1\ X_2—O_2—Y_1\ Y_2—O_3—Z_1\ Z_2—O_4, \text{ and}$$

$$O_1—X_1\ X_2—O_2—Y_1\ Y_2—O_3—Z_1\ Z_2—O_4—W_1\ W_2—O_5,$$

wherein $O_1, O_2, O_3, O_4,$ and $O_5$ are oligonucleotide moieties and $X_1, X_2; Y_1, Y_2; Z_1, Z_2,$ and $W_1, W_2$ are pairs terminal binding moieties.

4. The polynucleotide binding composition of claim 1 with the formula:

$$O_1—X_1\ X_2—O_2,$$

---

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 12 nucleotides
( B ) TYPE: nucleic acid
( C ) STRANDEDNESS: single
( D ) TOPOLOGY: linear ( x i ) SEQUENCE DESCRIPTION: SEQ ID NO: 1:

CGCTGAAGGG CT         12

( 2 ) INFORMATION FOR SEQ ID NO: 2:

( i ) SEQUENCE CHARACTERISTICS:
( A ) LENGTH: 14 nucleotides
( B ) TYPE: nucleic acid
( C ) STRANDEDNESS: single
( D ) TOPOLOGY: linear ( x i ) SEQUENCE DESCRIPTION: SEQ ID NO: 2:

TCTTCCTTAT TGAT       14 wherein $O_1$ and $O_2$ are oligonucleotide moieties and $X_1$ and $X_2$ are a pair of terminal binding moieties.

5. The polynucleotide binding composition of claim 3 wherein said short flexible linker is selected from the group consisting of phosphate, phophoramidate, hydroxyurethane, carboxyaminoalkyl and carboxyaminoalkylphosphate.

6. The polynucleotide binding composition of claim 3 wherein one or more of said pairs of terminal binding moieties form a hydrophobic complex.

7. The polynucleotide binding composition of claim 6 wherein $X_1$, $X_2$, $Y_1$, $Y_2$, $Z_1$, $Z_2$, $W_1$, and $W_2$ are selected from the group consisting of alkanes, fatty acids, fatty alcohols, steroids, waxes, and fat-soluble vitamins, wherein said $X_1$, $X_2$, $Y_1$, $Y_2$, $Z_1$, $Z_2$, $W_1$, and $W_2$ has no more than 20 to 40 carbon atoms.

8. The polynucleotide binding composition of claim 7 wherein $X_1$, $X_2$, $Y_1$, $Y_2$, $Z_1$, $Z_2$, $W_1$, and $W_2$ are each cholesterol.

9. The polynucleotide binding composition of claim 4 wherein $X_1$ is a steroid and $X_2$ is asteroid.

10. The polynucleotide binding composition of claim 9 wherein said steroids are cholesterol molecules.

11. The polynucleotide binding composition of claim 9 wherein said oligonucleotide moieties are antisense oligonucleotides complementary to a c-myc gene.

12. A polynucleotide binding composition of claim 9 wherein said steroids are chloesterol molecules attached to said short flexible linker at $C_3$ positions.

13. The polynucleotide binding composition of claim 5 wherein said short flexible linker is either carboxyaminoalkyl or carboxyaminoalkyl phosphate containing 2 to 8 carbon atoms.

* * * * *